US00PP08282P

United States Patent [19]

Fischer

[11] Patent Number: Plant 8,282

[45] Date of Patent: Jun. 29, 1993

[54] AFRICAN VIOLET PLANT NAMED MARA

[76] Inventor: Arnold W. Fischer, Kahlendamm 22, 3000 Hannover 51, Fed. Rep. of Germany

[21] Appl. No.: 771,196

[22] Filed: Oct. 4, 1991

[51] Int. Cl.[5] ..... A01H 5/00

[52] U.S. Cl. ..... Plt./69.2

[58] Field of Search ..... Plt./69.2, 69.1

[56] References Cited

U.S. PATENT DOCUMENTS

P.P. 5,025 4/1983 Holtkamp ..... Plt. 69.2
P.P. 5,543 8/1985 Fischer ..... Plt. 69.1
P.P. 6,480 12/1988 Holtkamp ..... Plt. 69.2

*Primary Examiner*—James R. Feyrer
*Assistant Examiner*—E. F. McElwain
*Attorney, Agent, or Firm*—Burns, Doane, Swecker & Mathis

[57] ABSTRACT

A new and distinct cultivar of African violet named Mara is provided. This cultivar exhibits a compact rosette growth habit, dark green pubescent foliage, and forms in abundance on upright peduncles attractive single zygomorphic-rotate bicolored flowers which are medium violet-blue with white undulated petal margins. The plant advantageously has a very floriferous habit with the flowering continuing for many weeks following its onset. Dark green pubescent foliage is formed comprising oval leaves with a waxy overall surface, a repand and crenate margin, a broad apex, and a cordate base. Susceptibility to African violet diseases has not been observed to date.

1 Drawing Sheet

SUMMARY OF THE INVENTION

The present invention comprises a new and distinct cultivar of African violet plant, botanically known as *Saintpaulia ionantha,* and hereinafter referred to by the cultivar name Mara.

The new cultivar was the product of a planned breeding program and was referred to during the breeding and selection process by the designation 087-225-013. The basic objective of the breeding program was to create an attractive new bicolored African violet cultivar having an abundance of medium violet-blue flowers possessing white undulated petal margins which are borne on upright peduncles above dark green foliage, and a compact growth habit.

The new cultivar was originated from a cross made in a controlled breeding program at Hannover, Germany. The female parent (i.e., the seed parent) was a cultivar designated 084-122-007, and the male parent (i.e., the pollen parent) was a cultivar designated 085-003-031. The discovery and selection of the new cultivar within the progeny of the stated cross occurred during 1987 in a controlled environment at Hannover, Germany.

Asexual reproduction of the new cultivar by leaf cuttings, as performed by me at Hannover, Germany and at Fallbrook, Calif., U.S.A. has demonstrated that the combination of characteristics as herein disclosed for the new cultivar are firmly fixed and are retained through successive generations of asexual propagation.

Mara has not been observed under all possible environmental conditions to date. Accordingly, the phenotype may vary significantly with variations in environment, such as temperature, light intensity, day length, plant nutrition etc.

The observations, measurements and values expressed herein describe the new cultivar when grown under greenhouse conditions at Hannover, Germany. These conditions are believed to closely approximate those commonly used in commercial practice.

The following traits have been repeatedly observed and are determined to be basic characteristics of Mara which in combination distinguish it as a new African violet cultivar:

(a) forms attractive bicolored medium violet-blue single zygomorphic-rotate flowers having white undulated petal margins,
(b) forms dark green pubescent foliage comprising oval leaves with a wavy overall surface, a repand and crenate margin, a broad apex, and a cordate base,
(c) exhibits a compact rosette growth habit with the flowers being held erect above the foliage on upright strong greyed-red peduncles at the center of the plant, and
(d) exhibits a very floriferous habit with flowers continuing to open for many weeks after the onset of flowering.

Each full blooming plant of the Mara cultivar commonly carries up to 15 or more flower stems with each stem commonly carrying 7 to 10 or more flowers. After the onset of flowering, the flowers commonly continue to open for approximately 6 to 8 weeks. Each individual flower commonly lasts approximately 3 to 4 weeks and after reaching maturity the flowers are substantially non-dropping and tend to dry up on the peduncle.

The flowers commonly exhibit a diameter of approximately 3.5 to 4.0 cm. and sometimes possess petaloid anthers. When started as 6 to 8 leaf-stage plantlets, Mara commonly finishes in 10 to 12 weeks when grown in 9 to 10 cm. pots depending on the growing conditions encountered.

Mara can be readily distinguished from the Nassau cultivar (U.S. Plant Pat. No. 6,480). Mara commonly begins flowering approximately 8 to 9 weeks after potting, while Nassau commonly begins flowering 9 to 10 weeks after potting. Unlike Mara, the parents of Nassau are D198/5 Blue Single (female) and GG 18 Blue Star (male). Mara commonly forms up to 15 or more flower stems with each carrying approximately 7 to 10 flowers, while Nassau commonly forms up to 10 or more flower stems with each carrying approximately 8 to 12 flowers.

Mara finishes in approximately 10 to 12 weeks when grown in 9 to 10 cm. pots, while Nassau is saleable 9 to 10 weeks after potting. The peduncle of Mara is Greyed-Red Group 178B, while that of Nassau is dark brown. Some of the flowers of Mara commonly possess petaloid anthers. The Mara plant commonly is approximately 8 to 9 cm. tall and approximately 23 to 25 cm. in diameter, while the Nassau plant commonly is approximately 7 to 10 cm. tall and 22 cm. in diameter. The Mara leaves are oval-shaped with an overall wavy surface, a repand and crenate margin, a broad apex and a cordate base. This can be compared to the heart-shaped leaves of Nassau. The Mara leaf coloration is Green Group 139A on the upper surface and Red-Purple Group 70A on the under surface. This can be compared to Nassau where the upper leaf surface of Yellow-Green Group 147A and the under leaf surface is greenish-purple with Yellow-Green Group 145D. The Mara flowers are bicolored, and on the upper surface are Violet-Blue Group 96C and lighter with white undulated margins of White Group 155A, and on the under surface a Violet-Blue Group 97A. In contrast, the Nassau flowers are, on the upper surface, between Violet-Blue Group 94B and 94C, and the under surface are 94C. The Mara style coloration is white, while that of Nassau is dark purple. Also, the pollen coloration of Mara is Yellow Group 4C, while that of Nassau is Yellow Group 7A.

BRIEF DESCRIPTION OF THE PHOTOGRAPH

The accompanying photograph shows as nearly true as it is reasonably possible to make the same, in a color illustration of this character, a typical specimen of a plant of the new cultivar. The plant of the new variety was grown in a greenhouse at Hannover, Germany. A typical specimen of the overall plant of the new cultivar is illustrated wherein the compact growth habit, foliage and blossoms are shown.

DETAILED DESCRIPTION

The chart used in the identification of the colors described hereafter is that of the Royal Horticultural Society (R.H.S. Colour Chart) except where general color terms of ordinary dictionary significance are expressed. The color values were taken under natural daylight conditions at 2:00 p.m. at Hannover, Germany.

Botanical classification: *Saintpaulia ionantha;* Ramat., cv. Mara.

Parentage:

*Female parent.*—084-122-007.

*Male parent.*—085-003-031.

Propagation: The new cultivar holds its distinguishing characteristics through successive propagations by leaf cuttings.

Plant: Commonly approximately 8 to 9 cm. tall when grown in pots, and approximately 23 to 25 cm. in diameter when fully grown. The growth rate of the plant is vigorous and the general shape of the fully grown plant is compact and rosette.

*Leaves.*—Quantity: Abundant. Shape: Oval-shaped with an overall wavy surface, a repand and crenate margin, a broad apex, and a cordate base. Size: Approximately 8 cm. in length on average-×approximately 7.5 cm. in width on average. Texture: Pubescent and glossy. Ribs and veins: Pinnate and well-pronounced red-purple on underside. Color — upper surface: Green Group 139A. Color — under surface: Red-Purple Group 70A. Petioles: Strong, hairy, Greyed-Red Group 178B.

*Flowers.*—Buds: Size: Approximately 0.5 cm. in diameter on average. Shape: Round. Rate of opening: Normal. Sepals: Shape: 5 in number, lanceolate. Color: Greyed-Red Group 178B. Phyllaries: Shape: 2 in number, lanceolate. Color: Green. Calyx: Size: Approximately 0.5 cm. in diameter on average. Shape: Funnel-shaped. Aspect: Pubescent. Peduncle: Length: Approximately 7.5 to 8.5 cm. on average. Character: Erect, rigid, hairy. Color: Greyed-Red Group 178B.

*Individual flowers.*—Number of petals: 5 in number, some flowers may include petaloid anthers. Size: A diameter of approximately 3.5 to 4 cm. and a depth of approximately 1 cm. commonly are exhibited. Shape: Single zygomorphic-rotate. Color — upper surface: Bicolored, Violet-Blue Group 96C and lighter with a margin of White Group 155A. Color — under surface: Violet-Blue Group 97A. The flower coloration can vary somewhat due to the amount of light, fertilizer, temperature and other growing conditions. Bearing: Cymose clusters on upright peduncles. Each peduncle commonly carries 7 to 10 or more flowers that are free-standing above the leaves thereby forming a compact bouquet of flowers. Flowering habit: Flowers profusely and intermittently throughout the year with blooms commonly lasting 3 to 4 weeks after which the petals dry up on the peduncle but commonly do not drop; finishes in approximately 10 to 12 weeks when a 6 to 8 leaf-stage plantlet is grown in a 9 to 10 cm. pot.

*Reproductive organs.*—Stamens: Borne singly on one side of the ovary; 2 anthers are basifixed. Anthers: 2 in number; monodelphous arrangement; approximately 0.2 cm. in length; yellow. Filaments: Approximately 0.3 to 0.4 cm. in length; yellow. Pollen color: Yellow, Yellow Group 4C. Pistils: Number: 1 in number. Styles: Approximately 0.5 to 0.7 cm. in length and white. Stigma: Sticky, white. Ovaries: Hypogynous and tomentose.

Disease resistance: No African violet disease has been observed to date.

General Observations

Mara is an attractive and vigorous but compact cultivar with dark green leaves and bicolored violet-blue flowers with white undulated petal margins. Out of the center of the plant commonly up to 15 or more strong flower stems appear with each commonly carrying 7 to 10 or more flowers. The flowers may include petaloid anthers and form an attractive free-standing bouquet above the leaves. Each individual flower commonly lasts approximately 3 to 4 weeks and is non-dropping. Plants of the Mara cultivar commonly are saleable approximately 10 to 12 weeks after potting.

I claim:

1. A new and distinct cultivar of African violet plant named Mara characterized by the following combination of characteristics:

(a) forms attractive bicolored medium violet-blue single zygomorphic-rotate flowers having white undulated petal margins, (b) forms dark green pubescent foliage comprising oval leaves with a wavy overall surface, a repand and crenate margin, a broad apex, and a cordate base, (c) exhibits a compact rosette growth habit with the flowers being held erect above the foliage on upright strong greyed-red peduncles at the center of the plant, and (d) exhibits a very floriferous habit with flowers continuing to open for many weeks after the onset of flowering;

substantially as herein shown and described.

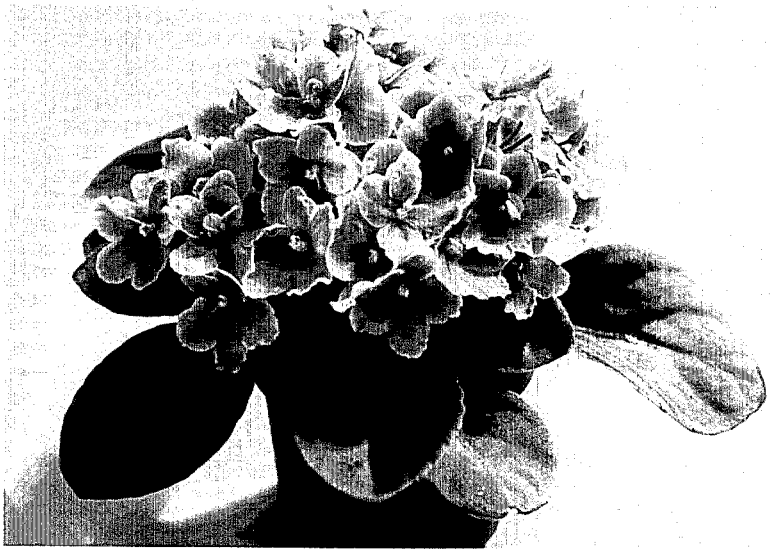

* * * * *